United States Patent
Yee et al.

(10) Patent No.: US 7,001,375 B2
(45) Date of Patent: Feb. 21, 2006

(54) METHOD AND APPARATUS FOR DETERMINING CHARACTERISTICS OF A LASER BEAM SPOT

(75) Inventors: Kingman Yee, San Jose, CA (US); Terrance N. Clapham, Jamestown, CA (US)

(73) Assignee: Advanced Medical Optics, Inc., Santa Clara, CA (US)

( * ) Notice: Subject to any disclaimer, the term of this patent is extended or adjusted under 35 U.S.C. 154(b) by 255 days.

(21) Appl. No.: 10/383,445

(22) Filed: Mar. 6, 2003

(65) Prior Publication Data

US 2003/0149426 A1    Aug. 7, 2003

Related U.S. Application Data

(62) Division of application No. 09/395,809, filed on Sep. 14, 1999, now Pat. No. 6,559,934.

(51) Int. Cl.
*A61F 9/01*        (2006.01)
(52) U.S. Cl. .................. 606/5; 606/4; 128/898
(58) Field of Classification Search ............... 356/121; 606/4–12
See application file for complete search history.

(56) References Cited

U.S. PATENT DOCUMENTS

| 4,713,537 | A | * | 12/1987 | Kunz et al. ............... 250/252.1 |
|---|---|---|---|---|
| 4,848,902 | A | | 7/1989 | Schickle et al. |
| 5,031,203 | A | | 7/1991 | Trecha |
| 5,059,021 | A | * | 10/1991 | Spence et al. ............... 356/121 |
| 5,078,491 | A | | 1/1992 | Johnston, Jr. |
| 5,144,630 | A | | 9/1992 | Lin |
| 5,267,012 | A | | 11/1993 | Sasnett et al. |
| 5,424,538 | A | | 6/1995 | Yoshino |
| 5,446,548 | A | | 8/1995 | Gerig et al. |
| 5,495,565 | A | | 2/1996 | Millard et al. |
| 5,694,209 | A | | 12/1997 | Alfille et al. |
| 5,742,626 | A | | 4/1998 | Mead et al. |
| 5,772,656 | A | | 6/1998 | Klopotek |
| 5,782,822 | A | | 7/1998 | Telfair et al. |
| 5,843,070 | A | | 12/1998 | Cambier et al. |
| 5,909,274 | A | | 6/1999 | Stucchi |
| 5,928,221 | A | | 7/1999 | Sasnett et al. |
| 5,999,550 | A | * | 12/1999 | Bellemore et al. ....... 372/38.02 |
| 6,090,102 | A | | 7/2000 | Telfair et al. |
| 6,138,503 | A | * | 10/2000 | Ray .......................... 73/105 |

(Continued)

FOREIGN PATENT DOCUMENTS

| JP | 59225320 A | 12/1984 |
|---|---|---|
| WO | WO 99/42885 A2 | 8/1999 |

OTHER PUBLICATIONS

Borsutzky, A. et al.; "Tunable UV Radiation at Short Wavelengths (188-240 nm) Generated by Sum-Frequency Mixing in Lithium Borate;" *Appl. Phys. B 52*; 1991; pp. 380-384.

*Primary Examiner*—Henry M Johnson, III
(74) *Attorney, Agent, or Firm*—Townsend and Townsend and Crew LLP

(57) ABSTRACT

A method of determining the dimensions of a laser beam spot, comprising: scanning the laser beam in a path across a reference-edge having a photodetector positioned therebehind; and measuring an output signal from the photodetector during the scanning, the output signal corresponding to an area of the laser beam spot incident on the photodetector during the scanning.

A method of aligning a laser beam delivery system, the method comprising: positioning a measurement/alignment tool at a target location; firing the laser beam on the tool; observing the laser beam using the tool; and adjusting the system in response to the sensed laser beam.

25 Claims, 14 Drawing Sheets

U.S. PATENT DOCUMENTS 6,195,164 B1 * 2/2001 Thompson et al. ......... 356/604
6,322,216 B1 11/2001 Yee et al.
6,331,177 B1 12/2001 Munnerlyn et al.
6,559,934 B1 5/2003 Yee et al.

* cited by examiner

METHOD AND APPARATUS FOR DETERMINING CHARACTERISTICS OF A LASER BEAM SPOT

CROSS-REFERENCES TO RELATED APPLICATIONS

This application is a divisional of and claims the benefit of priority from U.S. patent application Ser. No. 09/395,809, filed Sep. 14, 1999, now U.S. Pat. No. 6,559,934, the full disclosure of which is incorporated herein by reference.

TECHNICAL FIELD

The present invention relates to calibration techniques for determining the characteristics of a laser beam, particularly for use with laser eye surgery systems. More specifically, the invention provides devices, systems, and methods for determining the dimensions and/or position of the laser beam spot upon a target, and can provide input for generating, verifying, or adjusting ablation algorithms used to plan a resculpting procedure. When used in conjunction with laser eye surgery systems, the present invention can assist in determining patterns of laser beam spot delivery upon a patient's cornea, and can also be used in calibrating the laser beam delivery system.

BACKGROUND OF THE INVENTION

When performing laser eye surgery such as when ablating a target region on a patient's cornea with a refractive laser beam system, it is beneficial to have accurate information on the dimensions of the laser beam spot which is incident on the cornea. Deviation from a desired spot size and shape, such as by increased or decreased diameter of the laser beam spot or by the spot exhibiting an oval or non-symmetrical shape, could result in tissue ablation at undesired locations on the patient's corneas with each laser pulse, leading to less than ideal resculpting. Inaccuracy in the location of the laser spots may result in off-center ablations.

SUMMARY OF THE INVENTION

The present invention provides methods and apparati for determining characteristics of a laser beam spot, the characteristics typically including the intensity, dimensions, and/or position of the laser beam spot. An advantage of the present invention is that it can be used with laser eye surgery systems such that the dimensions of the laser beam spot, (including its diameter, area and eccentricity), can be precisely determined prior to, or concurrently with, the laser beam spot being used to ablate a region of the patient's cornea.

In preferred methods of the present invention, a laser beam is scanned in a path across a reference-edge, (which may preferably comprise a knife-edge), having a photodetector positioned therebehind, with the laser beam preferably remaining in a path generally perpendicular to the plane of the reference-edge during the scanning.

An output signal is generated by the photodetector corresponding to a percentage of the laser beam which is actually incident on the photodetector, (ie: not blocked by the reference-edge), at various moments in time during the scanning of the laser beam. For a beam having a uniform energy distribution, the percentage of the laser beam energy which is incident on the photodetector will correspond to the area of the laser beam spot which is incident on the photodetector. By measuring the output signal characteristics of the photodetector during the scanning, the present invention provides systems for determining the size and shape of the laser beam spot as well as the intensity of the laser beam. In preferred aspects, a computer calculates the intensity and shape profiles of the laser beam from the photodetector output signals.

As stated, the output signal generated by the photodetector will correspond to the size of the area of the laser beam spot incident thereon. As such, when the laser beam is fully incident on the reference-edge, (ie: when it is blocked from reaching the photodetector by the reference-edge), the photodetector will generate no output signal, or it will only generate a minimal output signal as a result of noise. Conversely, when the laser beam spot has been scanned completely across the reference-edge and is then fully incident on the photodetector, the photodetector will generate a maximum output signal.

The larger the area of the laser beam spot incident upon the photodetector, the stronger the output signal generated by the photodetector. Accordingly, in a preferred aspect of the invention, the intensity of the laser beam is determined by measuring the maximum output signal of the photodetector when the laser beam spot is fully incident on the photodetector and is not blocked by the reference-edge.

In another preferred aspect of the invention, the total area of the laser beam spot is determined by integrating the area under a curve representing the intensity of the photodetector signal output during the scanning as the laser beam is scanned across the reference-edge.

In yet another preferred aspect of the invention, the position of the center of the laser beam spot is located by determining when the output signal of the photodetector reaches half of its maximum output signal during the scanning, thus indicating that the center of the laser beam spot is positioned directly at the edge of the reference-edge, (with one half of the laser beam spot incident on the photodetector and one The larger the area of the laser beam spot incident upon the photodetector, the stronger the output signal generated by the photodetector. Accordingly, in a preferred aspect of the invention, the intensity of the laser beam is determined by measuring the maximum output signal of the photodetector when the laser beam spot is fully incident on the photodetector and is not blocked by the reference-edge.

In another preferred aspect of the invention, the total area of the laser beam spot is determined by integrating the area under a curve representing the intensity of the photodetector signal output during the scanning as the laser beam is scanned across the reference-edge.

In yet another preferred aspect of the invention, the position of the center of the laser beam spot is located by determining when the output signal of the photodetector reaches half of its maximum output signal during the scanning, thus indicating that the center of the laser beam spot is positioned directly at the edge of the reference-edge, (with one half of the laser beam spot incident on the photodetector and one half of the laser beam spot incident on the reference-edge).

In another preferred aspect of the present invention, the width of the laser beam spot in the direction of the path of the scanning is determined by locating the positions of the leading and trailing edges of the laser beam spot and then determining a spacing therebetween. In this aspect of the invention, the leading edge of the laser beam spot is located by determining when the photodetector begins to emit an output signal, (being indicative of the laser beam spot leading edge first passing over the reference-edge and becoming incident on the photodetector). The trailing edge of the laser beam spot is located by determining when the output signal of the photodetector has reached a maximum (indicating that the laser beam spot is not blocked by the reference-edge and is therefore fully incident on the photodetector). After determining the moments in time when the leading and trailing edges of the laser beam spot pass over the reference-edge as set out above, the width of the laser beam spot in the direction of the scanning is calculated based upon the speed of the laser beam scanning across the reference-edge.

In another preferred aspect of the present invention, the width of the laser beam spot in the direction of the path of the scanning is determined by locating the positions of the leading and trailing edges of the laser beam spot and then determining a spacing therebetween. In this aspect of the invention, the leading edge of the laser beam spot is located by determining when the photodetector begins to emit an output signal, (being indicative of the laser beam spot leading edge first passing over the reference-edge and becoming incident on the photodetector)., The trailing edge of the laser beam spot is located by determining when the output signal of the photodetector has reached a maximum (indicating that the laser beam spot is not blocked by the reference-edge and is therefore fully incident on the photodetector). After determining the moments in time when the leading and trailing edges of the laser beam spot pass over the reference-edge as set out above, the width of the laser beam spot in the direction of the scanning is calculated based upon the speed of the laser beam scanning across the reference-edge.

In other aspects of the present invention, asymmetries and eccentricities in the laser beam spot are found by measuring the rate of change or the symmetry of the rate of change of the output signal during the scanning.

In yet other aspects of the present invention, the size, shape and position of the laser beam spot are determined in two directions which are preferably perpendicular to one another. In this aspect of the invention, scanning is preferably performed in two perpendicular paths, over perpendicular first and second reference-edges. In this aspect of the invention, the size, shape and position of the laser beam spot are determined in the two perpendicular directions by measuring the output signals from either a single photodetector or two separate photodetectors positioned behind the reference-edges. An advantage of this aspect of the invention is that asymmetries of the beam spot (ie: an irregular shape of the beam spot) as well as eccentricities of the beam spot (ie: elongation of the beam spot to form an oval-shape), can be detected.

In preferred aspects of the present invention, the photodetector is a bulk detector. As such, an advantage of the present invention is that a more complex and expensive imaging detector is not required.

The present invention also provides methods of calibrating scanning laser beam delivery system. These methods comprise positioning a calibration tool at a target location; directing the laser beam onto the tool; sensing the laser beam using the tool; and adjusting the system in response to the sensed laser beam. In various aspects, the laser beam can be repeatedly re-directed, (for example, by a galvanometric mirror), between the tool and a patient's cornea. As such, after determining the size, shape and/or position of the beam, the laser beam can be applied at a known location on the cornea. Alternatively, the tool can be repeatedly inserted into and removed from the beam path between the laser beam source and the patient's cornea. As such, the alignment tool can then be repeatedly removed from the target location to allow for resculpting of the patient's cornea and then replaced at the target location after the resculpting of the cornea. Using either approach, a repetitive measurement of intensity and shape characteristics of the laser beam can be made as well as repetitive recalibration of the targeting of the laser beam can be achieved, thus ensuring precise positional accuracy when ablating the patient's cornea.

In still further aspects of the invention, the laser beam is split with a first portion of the beam directed to the measurement/alignment tool and a second portion directed to the patient's cornea such that real time measurement of shape and intensity characteristics of the laser beam spot and/or real time alignment of the laser beam delivery system can be achieved.

Regardless of the tool positioning, the calibration tool will often provide signals indicating beam spot size, shape, energy distribution, and/or location. These signals may be used to adjust the planned ablation protocol of the beam delivery system. Specifically, using the sensed information, an algorithm for calculating the locations and number of shots can be revised, thereby increasing the accuracy of the resculpting procedure. This calibration information can be used to adjust the ablation algorithm immediately before and/or during each ablation procedure.

In other aspects of the present invention, the measuring/alignment tool comprises a target which fluoresces in response to laser light incident thereon. In this second embodiment of the invention, an operator views the position of the fluoresced spot on the target screen while directing laser light at the target screen. Such viewing may preferably be done through the system microscope. The beam delivery system is aligned with the targeting optics, which may comprise a cross-hair reticle, thereby calibrating the laser beam delivery system.

DESCRIPTION OF THE SPECIFIC EMBODIMENTS

Figure 13:
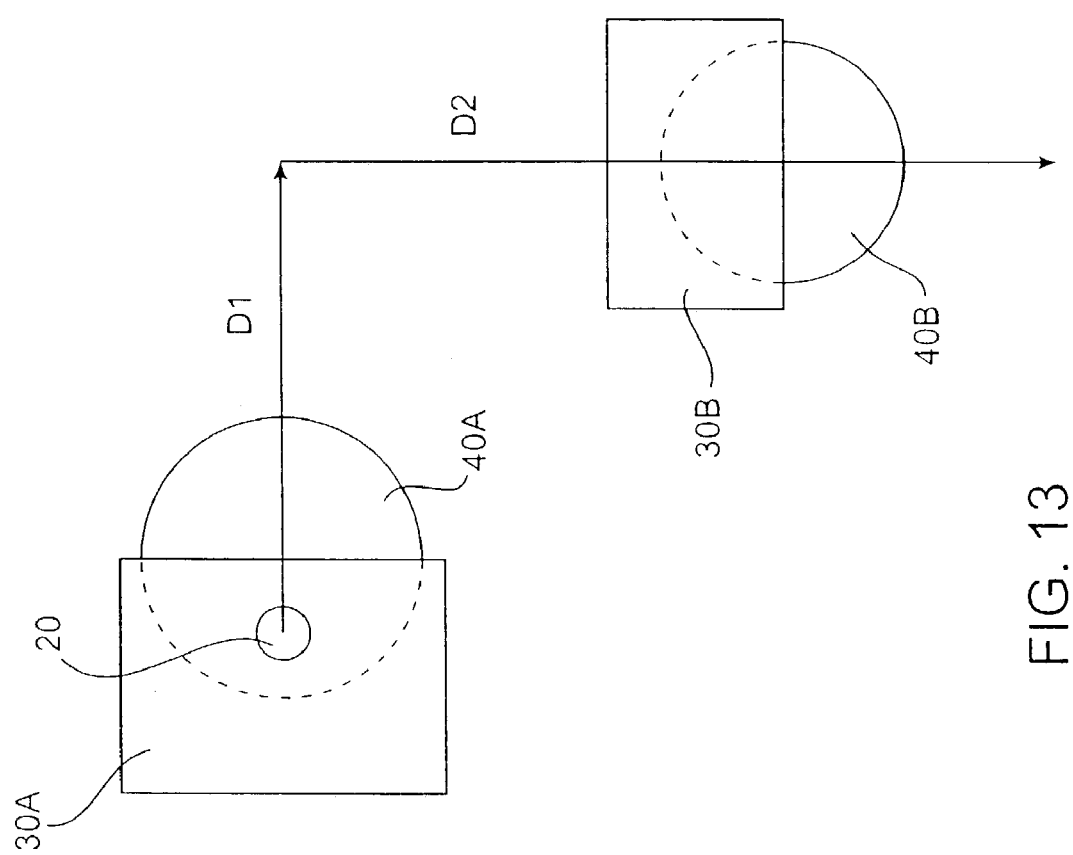
FIG. 13 is a top plan view showing a laser beam scanning over two perpendicular reference-edges, each reference-edge having a separate photodetector positioned therebehind.
Figure 14:
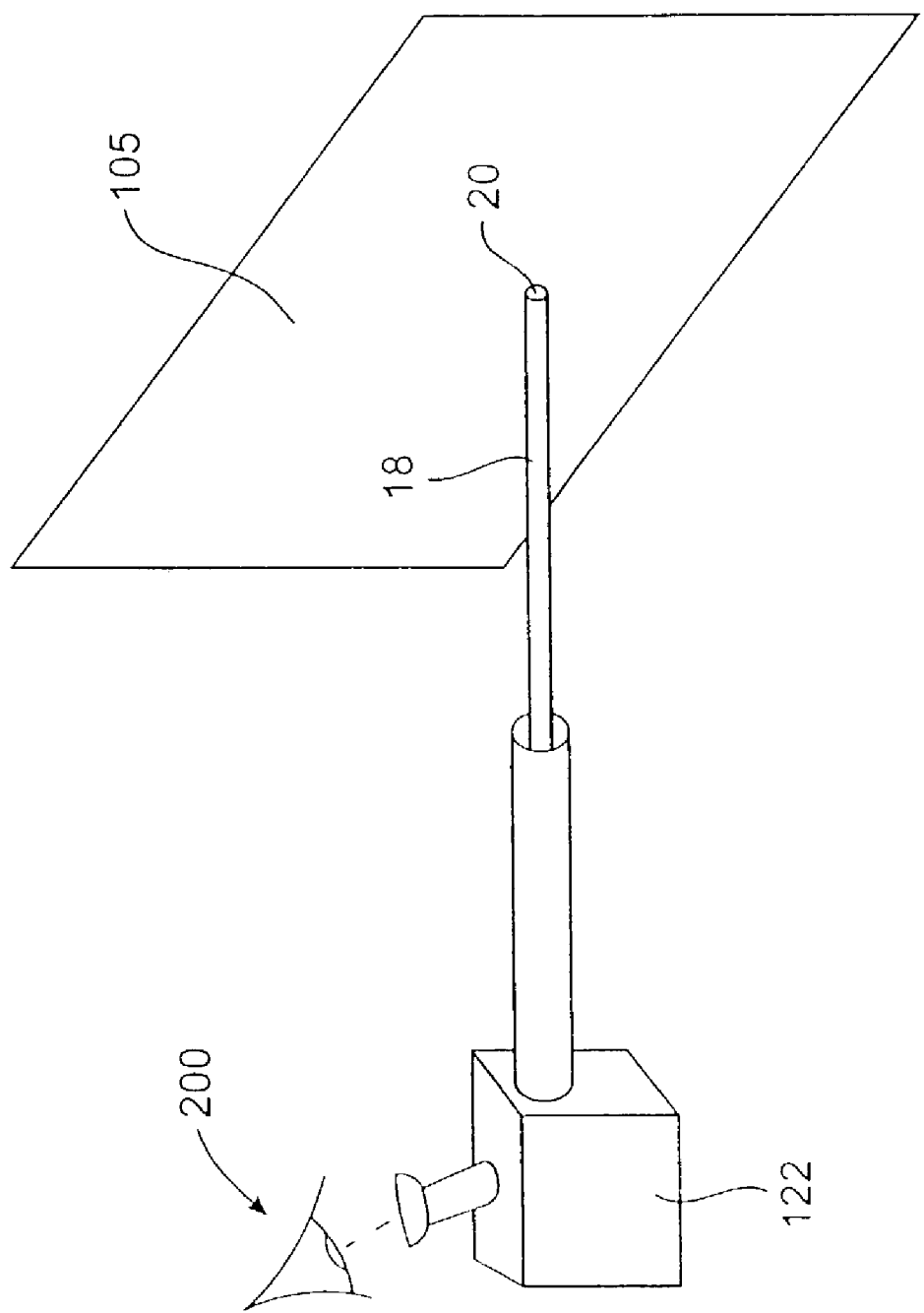
FIG. 14 is a perspective view of the laser beam delivery system directing a laser beam at a screen which fluoresces in the region where the laser beam is incident thereon.
Figure 15B:
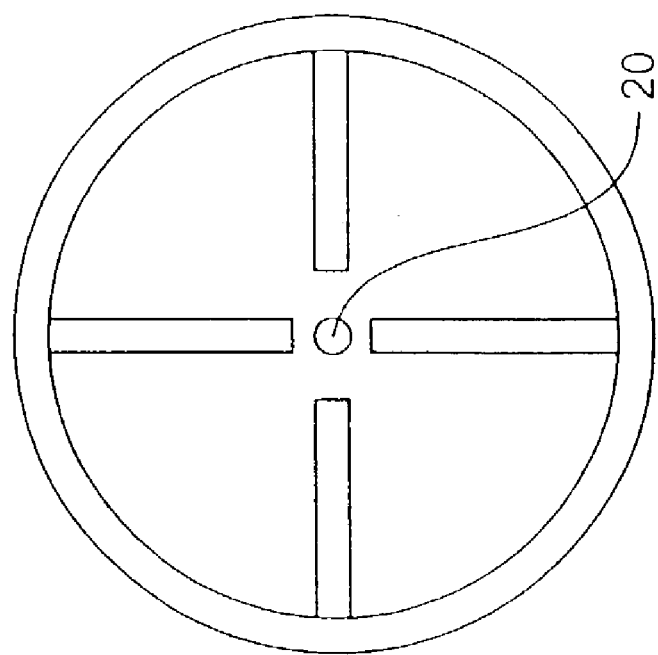
FIG. 15B is a view corresponding to FIG. 15A, after system calibration.

FIGS. 1 to 13 illustrate various aspects of a first embodiment of the present invention. FIGS. 14 to 15B illustrate various aspects of a second embodiment of the present invention. FIGS. 16 to 20 illustrate calibration systems which include a calibration tool which may comprise the first or second embodiment of the present invention.

When targeting an excimer laser beam to ablate regions of a patient's cornea during laser eye surgery, the spot formed by the laser beam upon the target will often have a circular shape, and will typically be intended to have a substantially uniform energy distribution. Other known beam delivery systems have rectangular or slit-shaped beams, optionally with Gaussian or other uneven energy profiles. Regardless, the exact intensity and shape profiles of the laser beam spot can not always be determined relying upon th targeting optics of the laser delivery system alone. It is beneficial to know the intensity and shape profiles of the laser beam as accurately as possible, especially when generating a pattern of laser beam spot application to the patient's cornea. Having accurate intensity and shape profile for the laser beam spot, it is possible to accurately sculpt the patient's cornea through successive application of a laser beam in a pattern of spots on the cornea. The present invention provides accurate determination of intensity and shape profiles of the laser beam spot which can be used to generate targeting patterns, and to otherwise calibrate the system.

The laser system may include, but is not limited to, an excimer laser such as an argon-fluoride excimer laser producing laser energy with a wavelength of about 193 nm. Alternative laser systems may include solid state lasers, such as frequency multiplied solid state lasers, flash-lamp and diode pumped solid state lasers, and the like. Exemplary solid state lasers include UV solid state lasers producing wavelengths of approximately 193–215 nm such as those disclosed in U.S. Pat. Nos. 5,144,630, and 5,742,626, and in Borsuztky et al., "Tunable UV Radiation at Short Wavelengths (188–240 nm) Generated by Frequency Mixing in Lithium Borate," *Appl. Phys.* 61:529–532 (1995). A variety of alternative lasers might also be used. The laser energy will often comprise a beam formed as a series of discreet laser pulses or shots.

Figure 19:
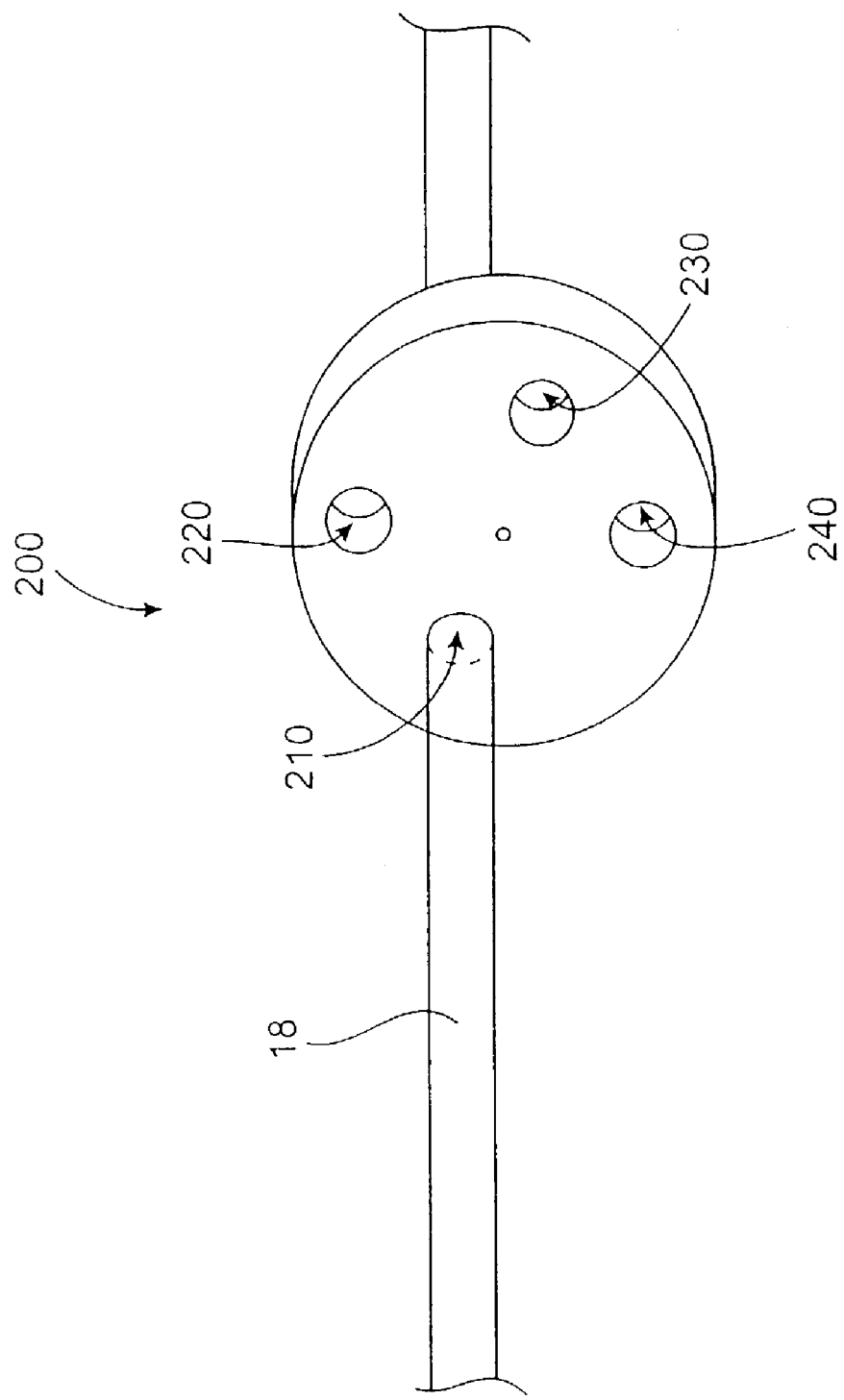
FIG. 19 is an illustration of the laser beam delivery system directing a laser beam through selectable apertures of an aperture wheel or turret.

The exact diameter and shape of the laser beam spot upon a target can not always be precisely determined relying upon the targeting system optics alone. This is especially true if the shape of the laser beam spot is somewhat eccentric or asymmetrical. Moreover, minor changes in the size and shape of the laser beam spot can be introduced when switching between different apertures and lenses in the laser delivery system. For example, FIG. 19 illustrates a laser beam 18 passing through an aperture 210 of an aperture wheel 200. As wheel 200 is rotated, laser beam 18 will pass through various apertures 220, 230 and 240. Each of apertures 210, 220, 230 and 240 may preferably be sized to different diameters such that different diameters of beam 18 can be selectively applied to the patient's cornea. The present invention provides systems which can determine the precise size and shape of beam 18 as it passes through each of apertures 210, 220, 230 and 240, as explained herein.

The present invention provides methods and apparati for precisely determining dimensions including the size, shape and position of the laser beam spot upon the target. Accordingly, laser beam spot shape and intensity profiles can be generated for use in sculpting the patient's cornea with a pattern of laser beam spots thereon. Also, the targeting optics of the laser delivery system can be aligned to account for any offset between the actual position of the laser beam as determined by the present invention and the position of the laser beam as determined by the scanning hardware and galvanometers of the laser delivery system's targeting optics. By determining the exact size, shape and intensity of the laser beam spot with the present invention, a desired corneal ablation treatment can be effected without the laser beam shots becoming incident on undesired locations of target tissue or underablating intended targets thereby enhancing the accuracy of the resculpting algorithm and procedure.

In the first embodiment of the present invention, as set out in FIGS. 1 to 13, the laser beam spot is scanned along a path which passes over a knife-edge, (or any other such reference-edge), having a photodetector positioned therebehind. Preferably, the laser beam is oriented perpendicular to the plane of the reference-edge during the scanning. In various approaches, the laser beam can be scanned across the reference-edge and onto the photodetector, or across the photodetector and onto the reference-edge.

By measuring the output of the photodetector, it is possible to determine the intensity, size, shape and position of the laser beam spot during the scanning, as follows.

Figure 1:
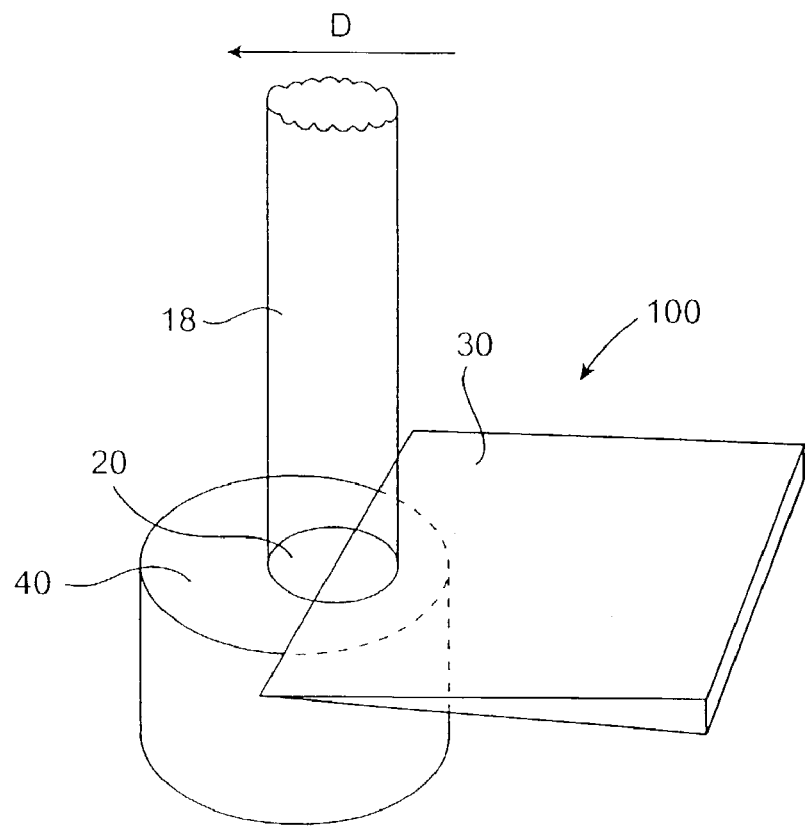
FIG. 1 is a perspective view of a laser beam being scanned over a reference-edge having a photodetector positioned therebehind at the moment in time when the laser beam is centered over the reference-edge.
Figure 16:
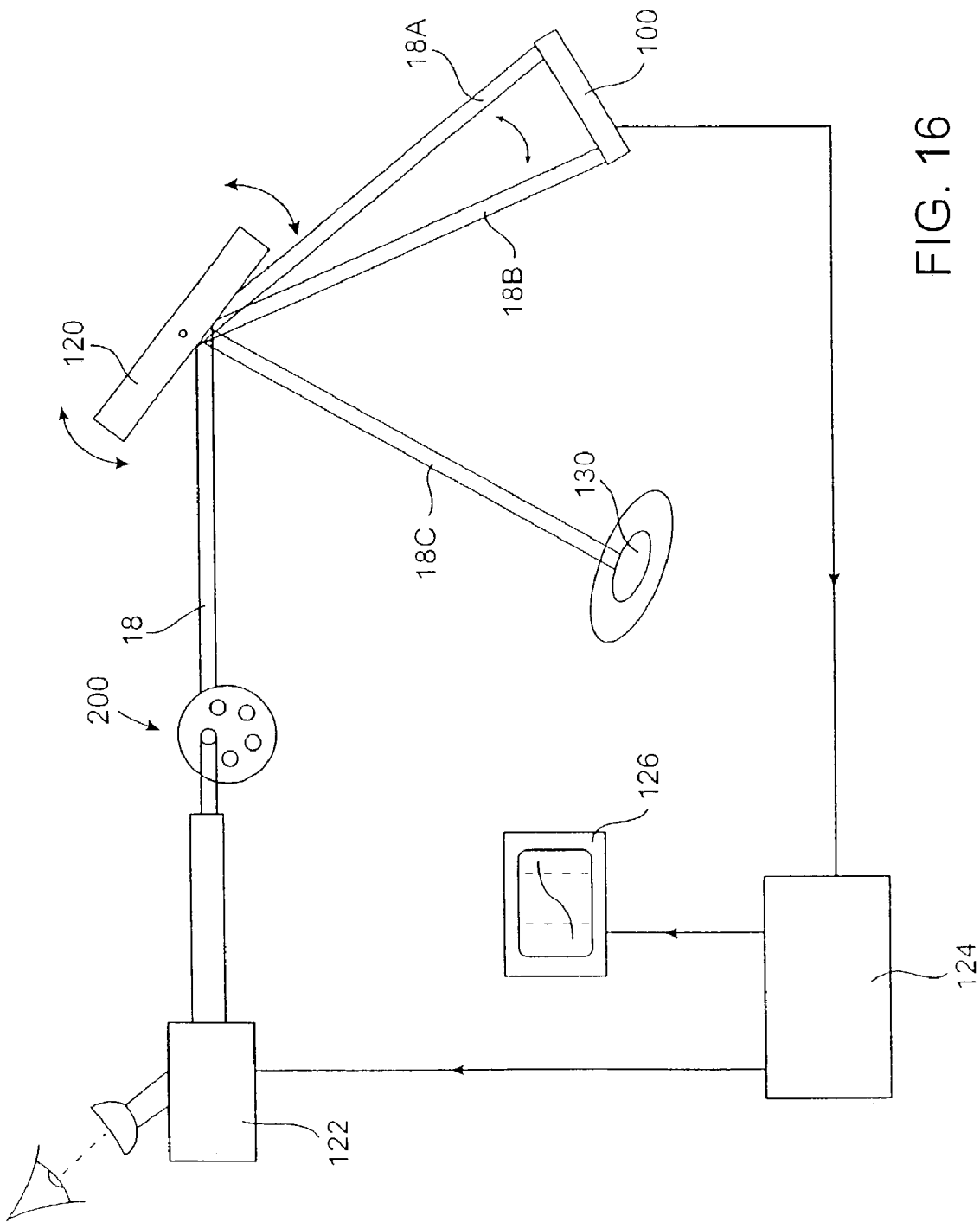
FIG. 16 is an illustration of the laser beam delivery system scanning a laser beam across a calibration tool and applying a therapeutic laser beam to a patient's cornea.

FIG. 1 shows a perspective view of a laser beam 18 which is directed downwardly from a laser source (not shown) towards a reference-edge 30 and photodetector 40. Laser beam 18 is "scanned", (ie: moved across, while remaining generally perpendicular to), a reference-edge 30 and photodetector 40. An example of scanning is shown in FIG. 16 in which laser beam 18 is scanned across a measurement/alignment tool 100, which may comprise reference-edge 30 and photodetector 40. Specifically, galvanometer 120 is rotated to scan laser beam 18 across the surface of alignment tool 100 from the position shown as beam 18A to the position shown as beam 18B.

Figure 2:
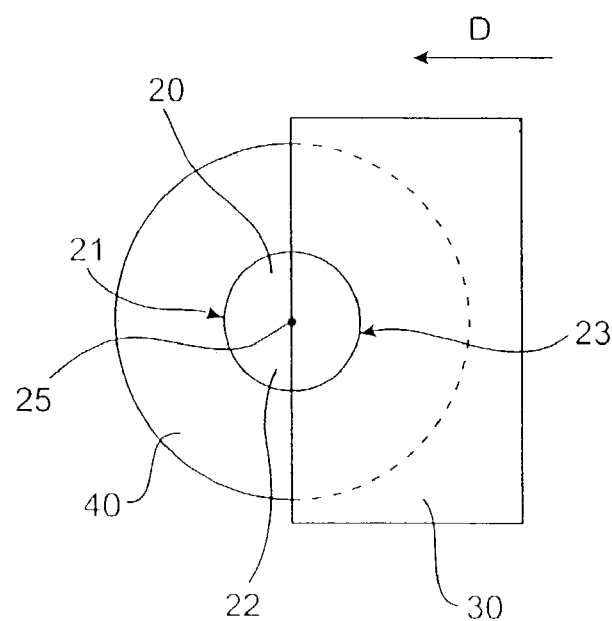
FIG. 2 is a top plan view corresponding to FIG. 1.

Returning to FIG. 1, laser beam 18 is thus scanned across reference-edge 30 and photodetector 40 in direction D. Photodetector 40, (which may preferably comprise a bulk photodetector), is positioned behind reference-edge 30 as shown. FIG. 2 shows a top plan view corresponding to FIG. 1 at the moment in time during the scanning where center 25 of laser beam spot 20 is positioned exactly at the edge of reference-edge 30. As can be seen, should laser beam spot 20 have a circular shape as illustrated, a first half 22 of laser beam spot 20 will be incident on photodetector 40 at the moment in time during the scanning where center 25 of laser beam spot 20 is positioned exactly over the edge of reference-edge 30.

Figure 3A:
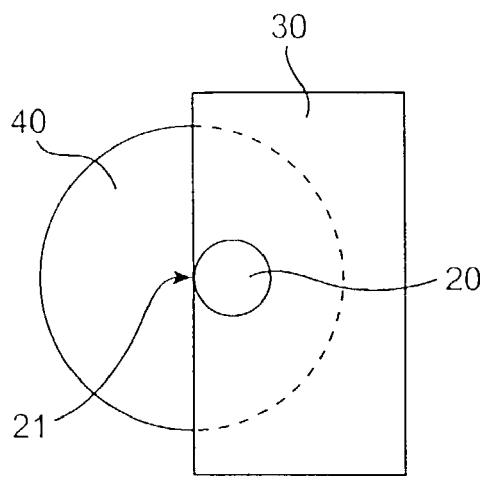
FIGS. 3A, 3B and 3C are sequential illustrations of the laser beam moving across the reference-edge of FIGS. 1 and 2.
Figure 3B:
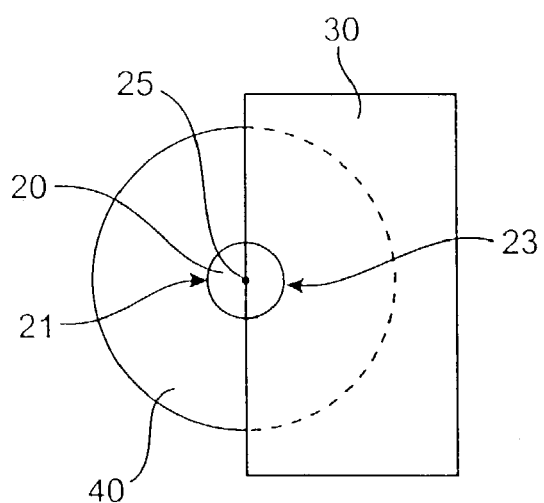
Figure 3C:
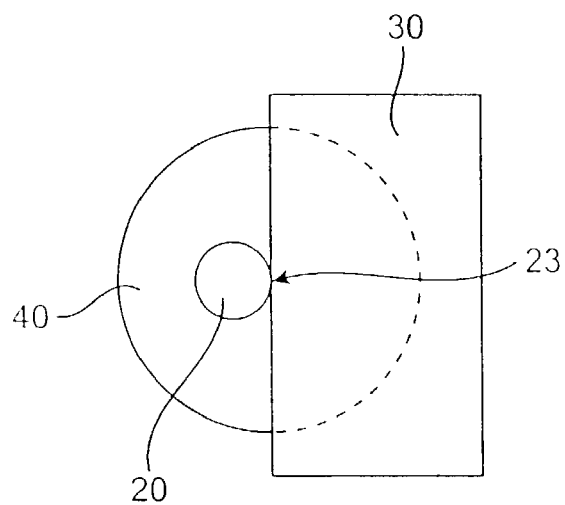
Figure 4:
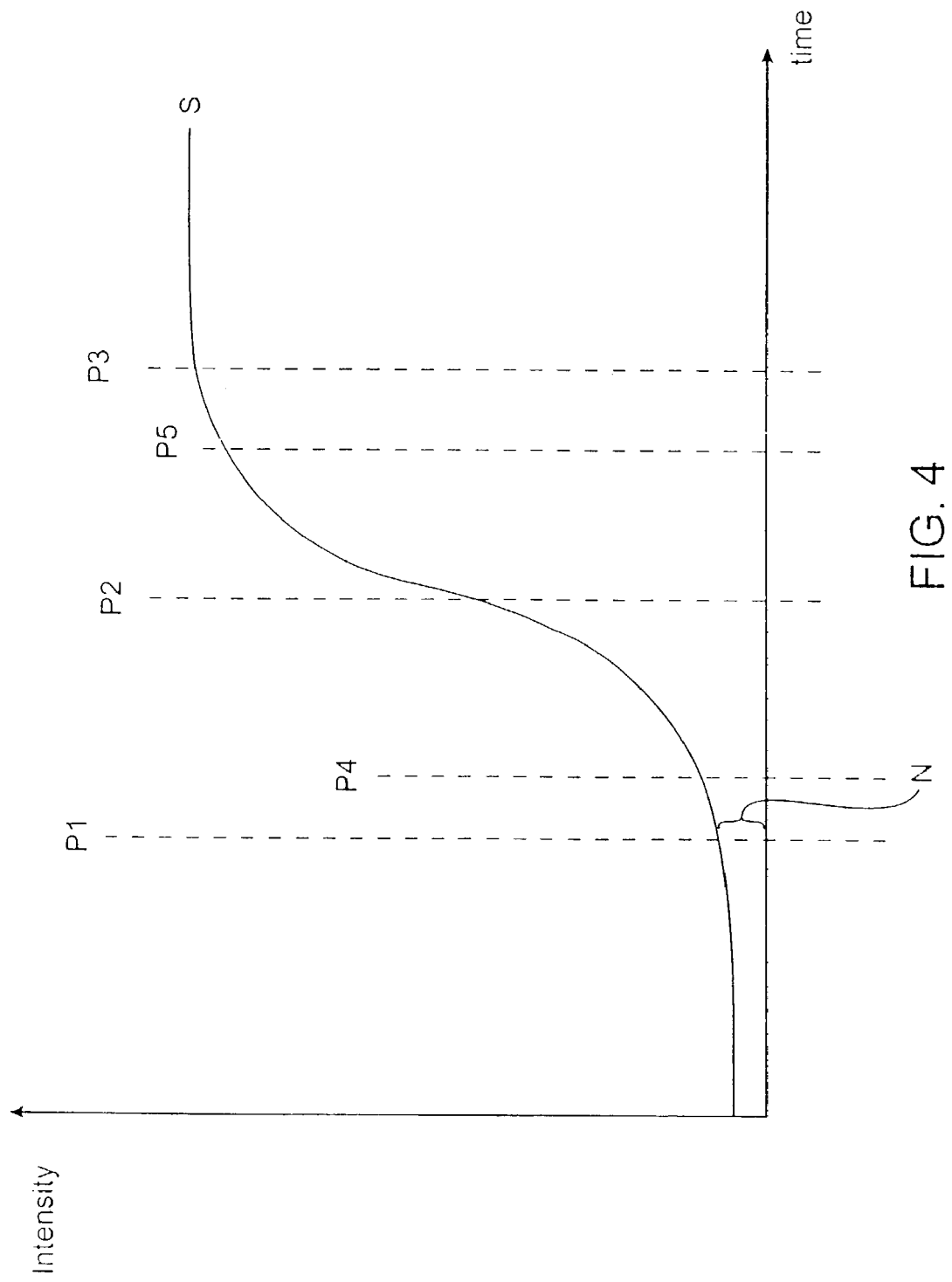
FIG. 4 is a graph of the output signal of the photodetector during the scanning illustrated in FIGS. 3A, 3B and 3C.

FIGS. 3A, 3B, and 3C show the sequential movement of laser beam spot 20 as laser beam 18 is scanned across reference-edge 30 and onto photodetector 40 during the scanning. FIG. 4 shows the corresponding intensity of output signal S from photodetector 40 taken over time during the scanning of beam spot 20 across reference-edge 30 and onto photodetector 40. The intensity of output signal S of photodetector 40 will correspond to the area of beam spot 20 which is not blocked by reference-edge 30 and is therefore directly incident on photodetector 40. Specifically, the intensity of signal S can be represented for a Gaussian pulse as follows:

$$S = \int_0^x (\text{spot intensity profile in } 2D) dx$$

or for a "top hat" pulse, (in which the energy distribution is substantially uniform across the cross-section of the pulse), as follows:

$$S = \int_0^x \sqrt{x^2 + y^2} dx$$

Points P1, P2 and P3 on FIG. 4 illustrate the intensity of output signal S at the moments in time when beam spot 20 is positioned as shown in FIGS. 3A, 3B and 3C respectively. For a generally circular beam spot 20, the intensity of output signal S will be in the shape of an S-shaped curve as shown in FIG. 4, as follows.

When beam spot 20 is positioned fully over reference-edge 30 as is shown in FIG. 3A, the photodetector will typically emit only a small signal intensity N, representing noise in the system. As beam spot 20 is scanned across reference-edge 30, progressively more of the area of the beam spot 20 will reach photodetector 40, increasing the intensity of the photodetector's output signal S. When beam spot 20 reaches the position illustrated in FIGS. 2 and 3B, such that center 25 of beam spot 20 is positioned directly at reference-edge 30, first half 22 of beam spot 20 will be incident upon the photodetector 40. Accordingly, signal S will reach approximately ½ of its maximum signal intensity at point P2. Finally, when beam spot 20 eventually reaches the position illustrated in FIG. 3C, at which the entire beam spot 20 is incident upon photodetector 40, signal S will reach its maximum signal intensity at point P3.

In a preferred aspect of the present invention, the intensity of laser beam 18 is determined by measuring the maximum output signal of the photodetector at point P3 when the laser beam spot is fully incident on the photodetector and is not blocked by the reference-edge.

In another preferred aspect of the present invention, the area of laser beam spot 20 is determined by taking the integral of the area under curve S between points P1 and P3 since this area will correspond to the full area of beam spot 20 which becomes incident upon photodetector 40 from the beginning of the scanning as shown in FIG. 3A to the end of the scanning as shown in FIG. 3C.

In another preferred aspect of the invention, the location of center 25 of laser beam spot 20 is determined. As explained above, center 25 of laser beam spot 20 passes over reference-edge 30 when the intensity of output signal S reaches point P2, being ½ of the intensity of output signal S at point P3. Due to the presence of a small noise signal N at point P1, it may be difficult to determine when the output signal intensity is at point P2. Accordingly, in a preferred approach, P2 is found by determining a point midway between a first fraction of the maximum signal output and a second fraction of the maximum signal output, wherein the first and second fractions add together to the maximum signal output.

For example, a point P4 is located where the signal intensity equals 10% of the maximum signal output at point P3. Similarly, a point P5 is located where the signal intensity equals 90% of the maximum signal output at point P3. After locating points P4 and P5 on the signal curve, point P2 is then located centrally therebetween. It is to be appreciated that points P4 and P5 could also be 30% and 70%, or 15% and 85%, or any other combination of respective percentages which add together to 100% of the maximum signal intensity at point P3.

The speed of the scanning can be known either through position feedback systems or by determining the speed and time of the scanning. Knowing the speed of the scanning, (which corresponds to the rate of rotation of galvanometer 120), and determining the moment in time at which P2 is reached, (ie: when the center 25 of beam spot 20 is positioned at reference-edge 30), the location of center 25 is thus determined.

In another preferred aspect of the present invention, the width of beam spot 20 in scanning direction D is determined as follows. Referring first to FIG. 3A, a leading edge 21 of beam spot 20 is positioned at reference-edge 30, (as represented by point P1 in FIG. 4). At the commencement of scanning, leading edge 21 will start to become incident upon photodetector 40, (as represented in FIG. 4 by the output signal intensity of the photodetector just beginning to increase). Referring to the end of the scanning as shown in FIG. 3C, a trailing edge 23 will become incident upon photodetector 40 as shown, (as represented by point P3 in FIG. 4 when the output signal intensity of the photodetector stops increasing).

Knowing the speed of movement of laser beam scanning in direction D, (either by knowing the speed and time during the scanning or through a position feedback system), the moments in time when P1 and P3 are reached can be determined. As such, the width of laser beam spot 20, (which begins its passage over photodetector 40 at point P1 and ends passage at point P3), can easily be calculated.

In other preferred aspects of the invention, the shape of the laser beam spot 20 is determined by measuring the rate of change of output signal S during the scanning.

Figure 6:
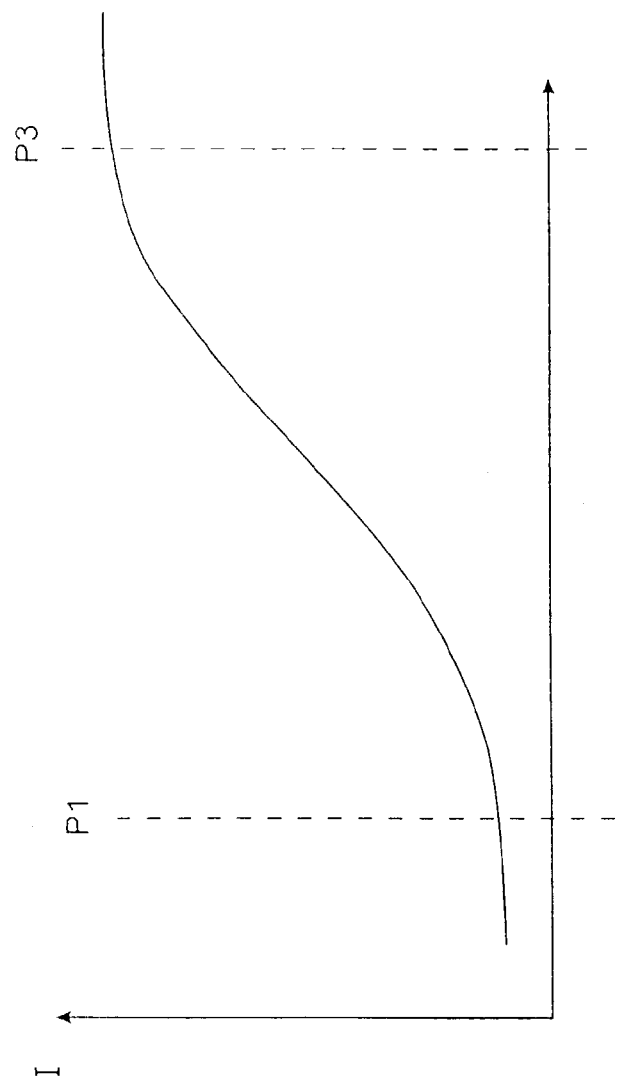
FIG. 6 is a representation of the output signal of the photodetector during a scanning of the oval shaped laser beam spot of FIG. 5.
Figure 5:
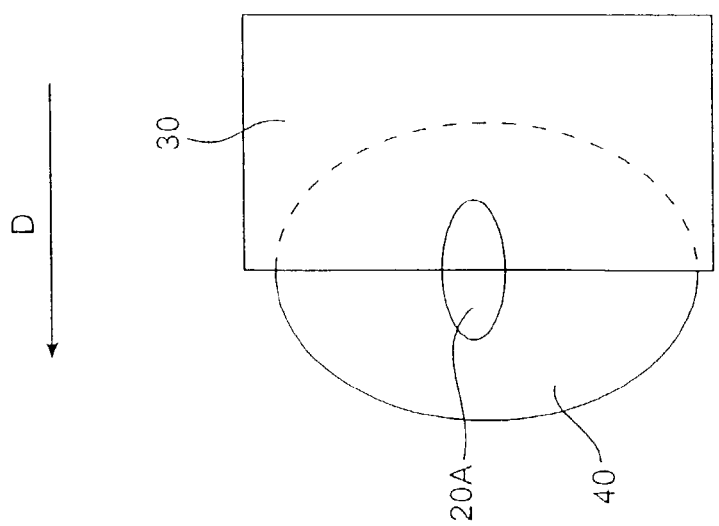
FIG. 5 is a view of an oval shaped laser beam spot, (having a major axis parallel to the path of the scanning), being scanned over a reference-edge with a photodetector positioned therebehind.

For example, FIG. 5 illustrates an oval shaped laser beam spot 20A being scanned across reference-edge 30 and photodetector 40. Laser beam spot 20A is elongated in direction D, as shown. The intensity of the output signal S corresponding to scanning laser beam spot 20A across reference-edge 30 and photodetector 40 is shown in FIG. 6. As can be seen, the rate of change of the output signal S of photodetector 40 between points P1 and P3 is more gradual than was illustrated in FIG. 4, (shown by the greater amount of time separating points P1 and P3 in FIG. 6 as compared to FIG. 4). The more gradual the rate of change of the output signal S in FIG. 6 thus indicates that laser beam spot 20A is more elongated in direction D than circular-shaped laser beam spot 20.

Figure 8:
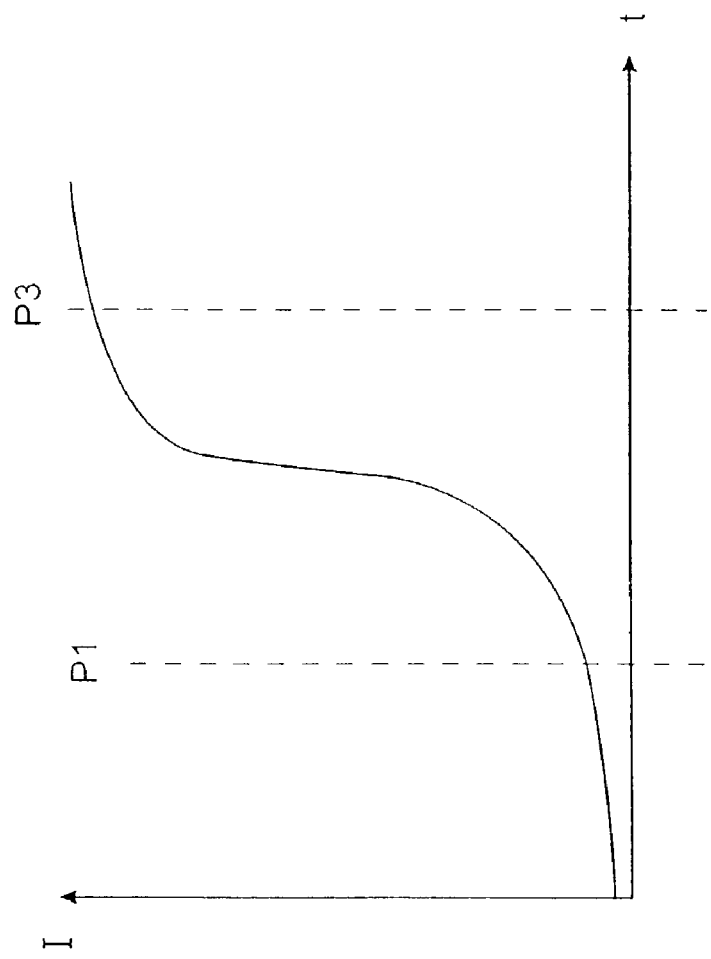
FIG. 8 is a representation of the output signal of the photodetector during a scanning of the oval shaped laser beam spot of FIG. 7.
Figure 7:
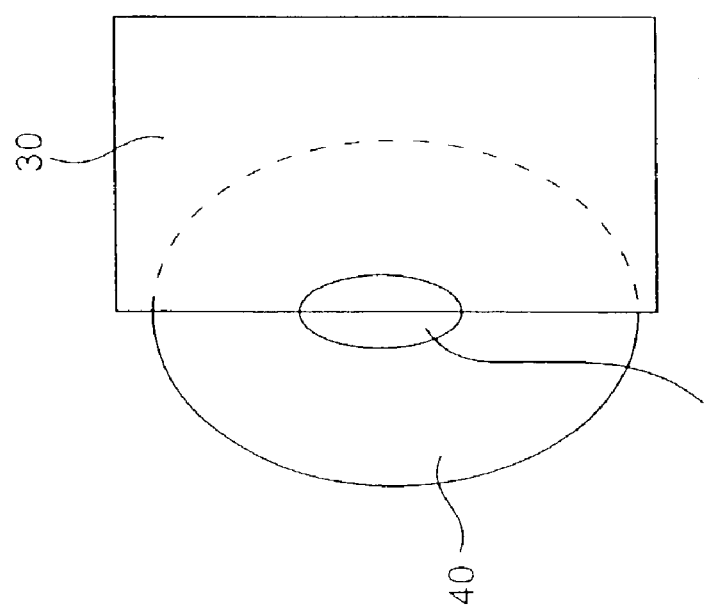
FIG. 7 is a plan view of an oval shaped laser beam spot, (having a major axis perpendicular to the path of the scanning), being scanned over a reference-edge with a photodetector therebehind.
Figure 10:
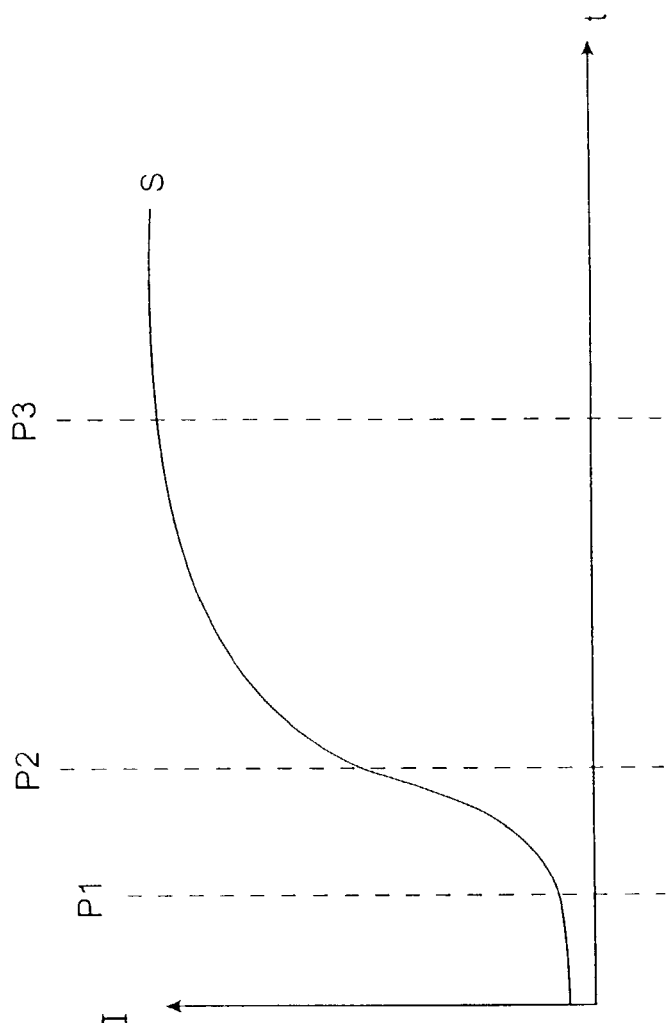
FIG. 10 is a representation of the output signal of the photodetector during a scanning of the oval shaped laser beam spot of FIG. 9.

Conversely, FIG. 7 illustrates an oval beam spot 20B, being scanned across reference-edge 30 and photodetector 40. Laser beam spot 20B is elongated in a direction perpendicular to direction D, as shown. FIG. 8 shows the intensity of output signal S corresponding to the scanning of FIG. 7. As can be seen, the rate of change of output signal S is much faster than was shown in FIG. 4, (as shown by the smaller amount of time between points P1 and P3 in FIG. 8 as compared to FIG. 4). The faster rate of change of the output signal S in FIG. 8 thus indicates that laser beam spot 20B is more elongated in a direction perpendicular to direction D than circular-shaped laser beam spot 20.

Figure 9:
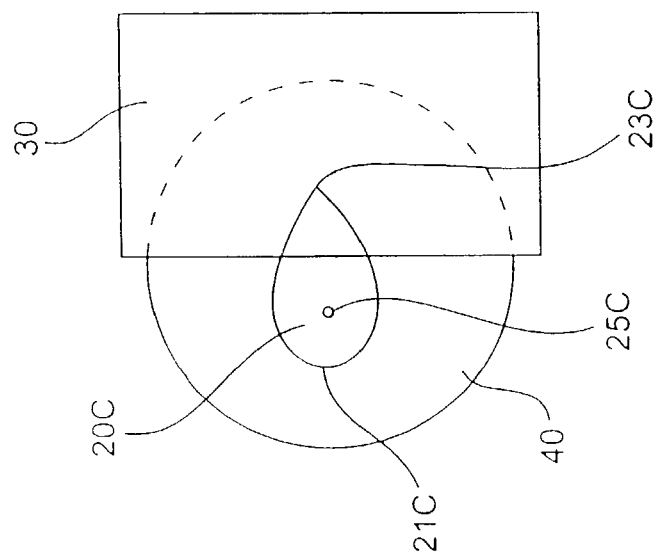
FIG. 9 is a plan view of an eccentric shaped laser beam spot being scanned over a reference-edge with a photodetector therebehind.

In another aspect of the present invention, the shape of laser beam spot 20 can be determined by measuring the symmetry of output signal S during the scanning. As such, asymmetries and/or eccentricities of laser beam spot 20 are determined as follows. Referring to FIG. 9, an eccentric exaggerated "teardrop-shaped" laser beam spot 20C is scanned across reference-edge 30 and photodetector 40. Using the novel approaches set out above, the leading edge 21C will be located at point P1, the spot center 25C will be located at point P2 and the trailing edge will be located at point P3 on FIG. 10. As can be seen, point P2 (at Conversely, FIG. 7 illustrates an oval beam spot 20B, being scanned across reference-edge 30 and photodetector 40. Laser beam spot 20B is elongated in a direction perpendicular to direction D, as shown. FIG. 8 shows the intensity of output signal S corresponding to the scanning of FIG. 7. As can be seen, the rate of change of output signal S is much faster than was shown in FIG. 4, (as shown by the smaller amount of time between points P1 and P3 in FIG. 8 as compared to FIG. 4). The faster rate of change of the output signal S in FIG. 8 thus indicates that laser beam spot 20B is more elongated in a direction perpendicular to direction D than circular-shaped laser beam spot 20.

In another aspect of the present invention, the shape of laser beam spot 20 can be determined by measuring the symmetry of output signal S during the scanning. As such, asymmetries and/or eccentricities of laser beam spot 20 are determined as follows. Referring to FIG. 9, an eccentric exaggerated "teardrop-shaped" laser beam spot 20C is scanned across reference-edge 30 and photodetector 40. Using the novel approaches set out above, the leading edge 21C will be located at point P1, the spot center 25C will be located at point P2 and the trailing edge will be located at point P3 on FIG. 10. As can be seen, point P2 (at Conversely, FIG. 7 illustrates an oval beam spot 20B, being scanned across reference-edge 30 and photodetector 40. Laser beam spot 20B is elongated in a direction perpendicular to direction D, as shown. FIG. 8 shows the intensity of output signal S corresponding to the scanning of FIG. 7. As can be seen, the rate of change of output signal S is much faster than was shown in FIG. 4, (as shown by the smaller amount of time between points P1 and P3 in FIG. 8 as compared to FIG. 4). The faster rate of change of the output signal S in FIG. 8 thus indicates that laser beam spot 20B is more elongated in a direction perpendicular to direction D than circular-shaped laser beam spot 20.

In another aspect of the present invention, the shape of laser beam spot 20 can be determined by measuring the symmetry of output signal S during the scanning. As such, asymmetries and/or eccentricities of laser beam spot 20 are determined as follows. Referring to FIG. 9, an eccentric exaggerated "teardrop-shaped" laser beam spot 20C is scanned across reference-edge 30 and photodetector 40. Using the novel approaches set out above, the leading edge 21C will be located at point P1, the spot center 25C will be located at point P2 and the trailing edge will be located at point P3 on FIG. 10. As can be seen, point P2 (at which signal intensity is ½ of that at P3), is not centered between points P1 and P3, but rather is closer to P1, thus indicating that laser beam spot 20C has a somewhat eccentric shape with its center 25C being closer to leading edge 21C than to trailing edge 23C.

As described above, the present invention provides systems for measuring the intensity, size and shape profiles of a laser beam spot in the direction in which it is scanned over a reference-edge and onto a photodetector.

Figure 11:
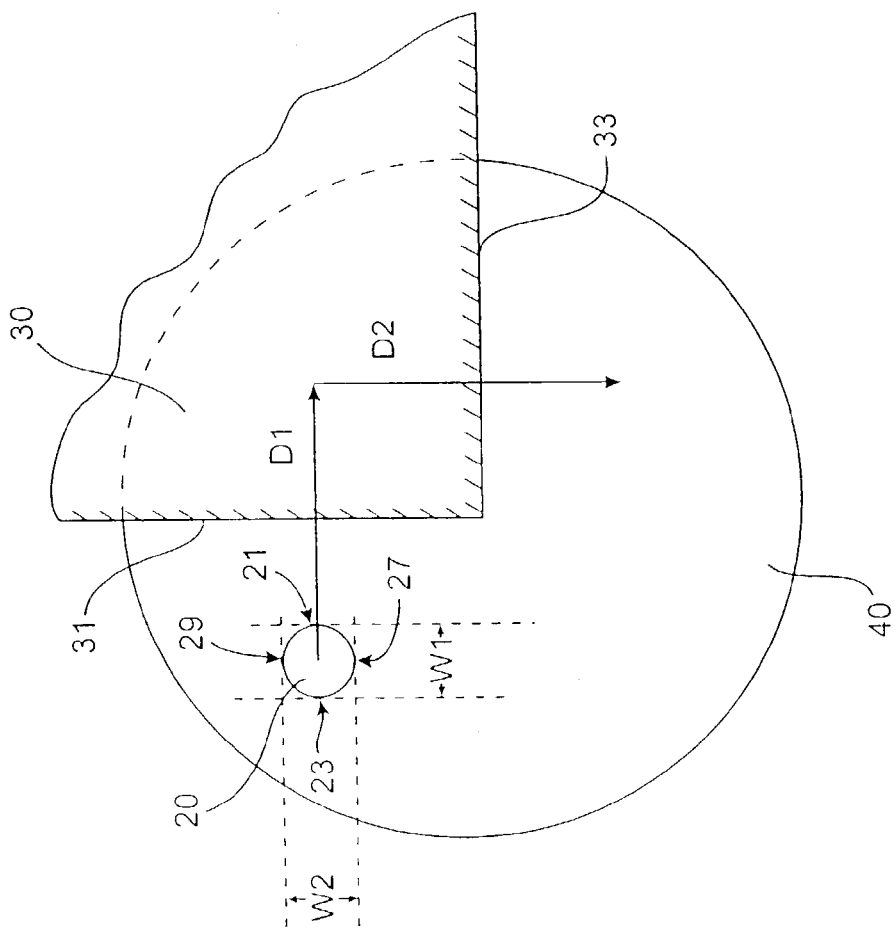
FIG. 11 is a top plan view of a laser beam spot being scanned over two perpendicular reference-edges wherein the two reference-edges together form a corner of a planar member.

In additional preferred aspects of the present invention, the size, shape and position of the laser beam spot are determined in two directions, as follows. Referring to FIG. 11, a beam spot 20 is moved in a first direction D1 across edge 31 followed by movement in a second perpendicular direction D2 across edge 33. In this illustration, edges 31 and 33 together form a corner to reference-edge 30.

Measuring the output signal of photodetector 40 as laser beam spot 20 is scanned across edge 31 using the above described techniques, the positions of leading edge 21, trailing edge 23 and center 25 can be determined. Knowing the positions of leading edge 21 and trailing edge 23, width W1 in direction D1 can be calculated. Subsequently, laser beam spot 20 is scanned in perpendicular direction D2 across edge 33. As a result, the positions of side edges 27 and 29, and center 25 can be determined using the above described techniques. Knowing the positions of side edges 27 and 29, width W2 in direction D2 can then be calculated.

Figure 12:
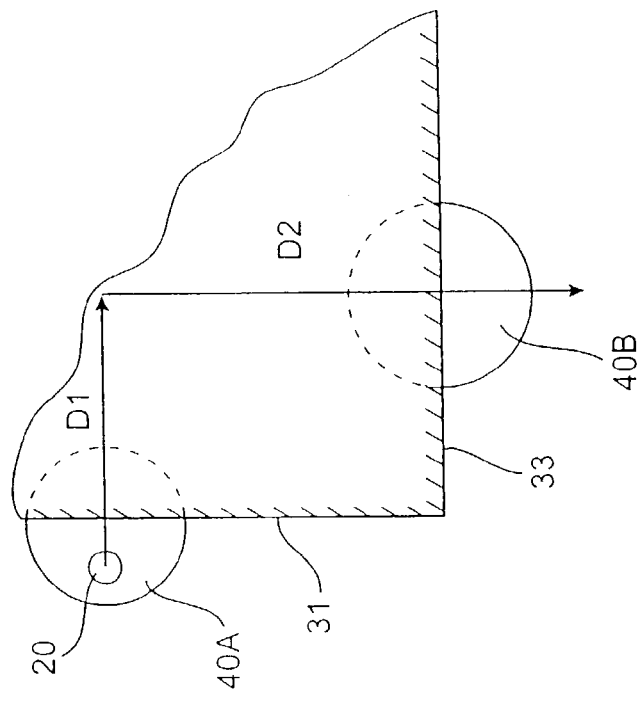
FIG. 12 corresponds to FIG. 11, but instead uses two separated photodetectors.

FIG. 12 illustrates an arrangement similar to that of FIG. 11, but instead using separate photodetectors 40A and 40B. FIG. 13 illustrates yet another arrangement, instead using two separate perpendicular reference-edges 32 and 34 and two separate photodetectors 40A and 40B positioned thereunder as shown.

After determining the size and shape of laser beam spot 20 upon photodetector 40, the laser beam can then be safely directed at target tissue in the cornea of a patient's eye, knowing the exact size and shape of the beam spot which will be incident upon the target tissue. Preferably, the cornea can be sculpted to a desired shape by repeated application of the laser beam to a number of different sites in a pattern on the cornea. Using the present invention, the size and shape of the laser beam spot can be precisely determined prior to, or concurrently with, successive applications of the laser beam to the cornea.

Figure 17:
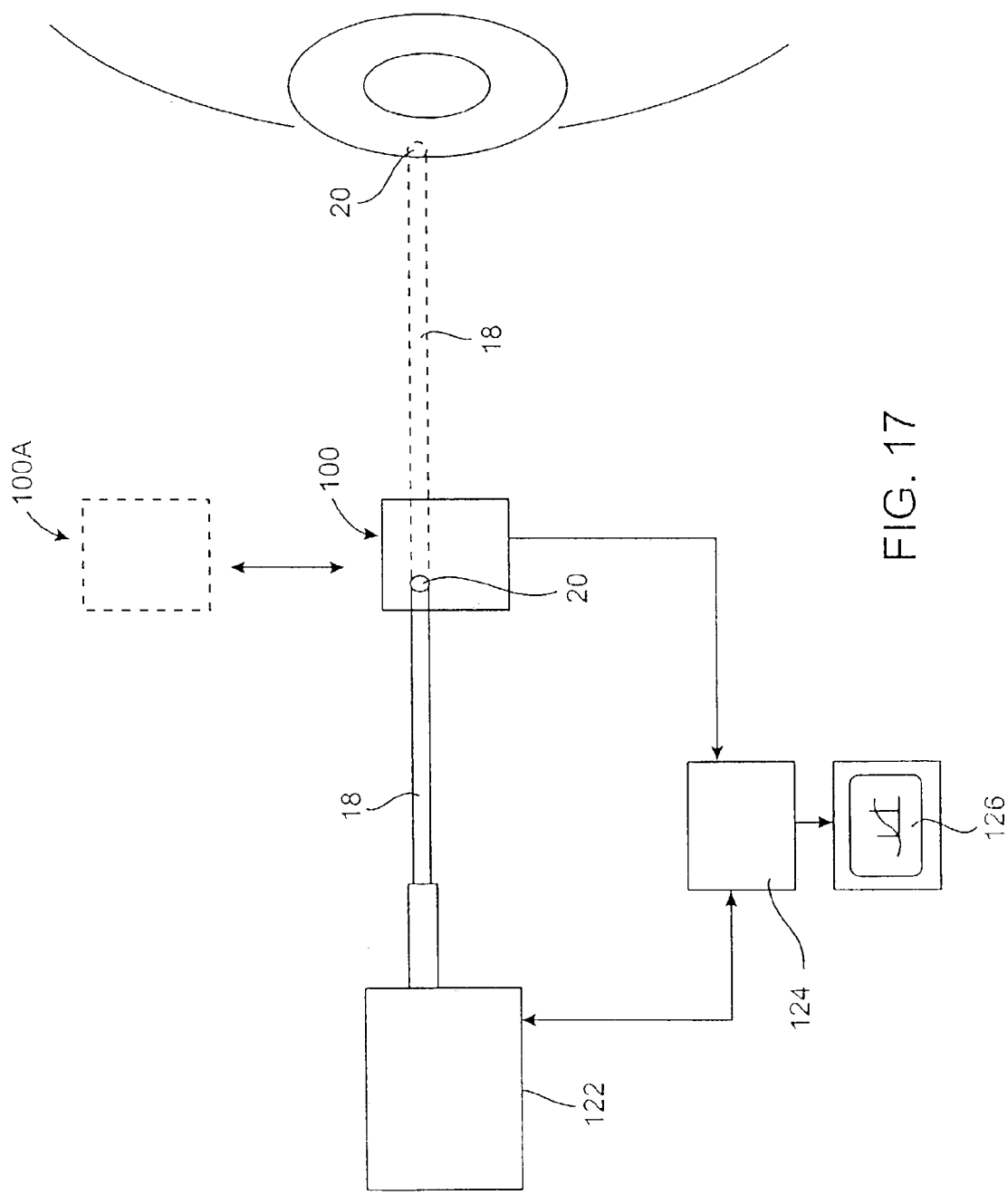
FIG. 17 is an illustration of the laser beam delivery system applying a therapeutic laser beam to a patient's cornea showing a removable calibration tool in the beam path.

For example, as shown in FIGS. 16 and 17, laser beam 18 can be alternatingly re-directed between a calibration tool 100 and the patient's cornea 130. Calibration tool 100 may preferably comprise reference-edge 30 and photodetector 40 operating as described above. Referring to FIG. 16, laser beam 18 can be repeatedly reflected as beam 18C by galvanometer 120 to a patient's cornea 130, (subsequently to the scanning of beam 18 across tool 100, from the position shown as beam 18A to 18B). Referring to FIG. 17, tool 100 can instead be repeatedly moved back and forth to the position shown in phantom as tool 100A. As such, laser beam 18 is periodically interrupted in its application on cornea 130 when tool 100 is positioned in the path of the laser beam to determine the intensity and shape profiles of laser beam spot 20. The process of repeatedly scanning beam 18 across alignment tool 100, or repeatedly removing and replacing tool 100 in the beam path, (thereby repeatedly determining the size and shape of laser beam spot 20), and then repeatedly re-sculpting cornea 130 by laser ablation ensures the size and shape of laser beam spot 20 do not change over time during the ablation of the patient's cornea.

Figure 18:
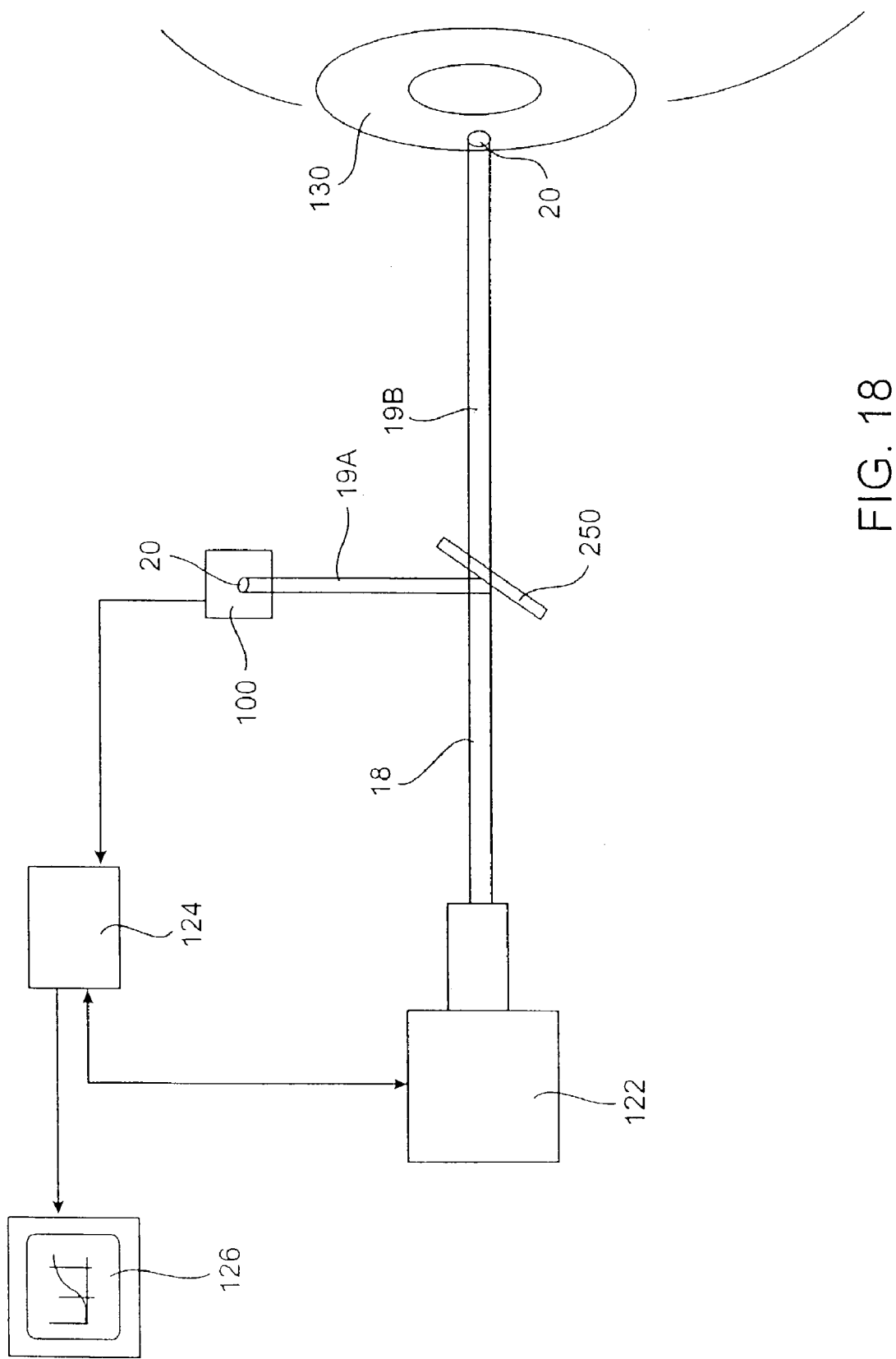
FIG. 18 is an illustration of the laser beam delivery system simultaneously applying a therapeutic laser beam to a patient's cornea and to a calibration tool.

As illustrated in FIG. 18, a beam splitter 250 can also be used to direct a first portion 19A of beam 18 to tool 100 while simultaneously directing a second portion 19B of beam 18 to cornea 130. Using the arrangement of FIG. 18, real time measurement of both intensity and shape profiles of beam spot 20 upon cornea 130 can be achieved while the tissues of the cornea are ablated.

Also shown in FIGS. 16, 17 and 18 are a computer 124 to record the intensity of the output signal of photodetector 40 over time, thereby generating both intensity and shape profiles of laser beam spot 20. Additionally, computer 124 is adapted to calculate preferred patterns of laser beam spot application on cornea 130 from the intensity and shape profiles of laser beam spot 20. As such, cornea 130 can sculpted to a desired shape. Additionally, a monitor 126 is adapted to display a waveform representing the intensity of the output signal of photodetector 40 over time.

In another preferred aspect, tool 100 can be used to align the targeting optics of the laser delivery system. Specifically, after locating center 25 of laser beam spot 20 as it is scanned across photodetector 40, the beam delivery system (including galvanometer 120) can be precisely aligned to compensate for any difference between the position of the laser beam as determined by targeting optics 122, and that indicated by tool 100. A suitable material for tool 100 which fluoresces but does not ablate is preferred. Such material may comprise a white stock paper or a white business card. Also, a suitable fluorescent plate material which can be purchased from Startech Inc, of Connecticut can be used.

Figure 15A:
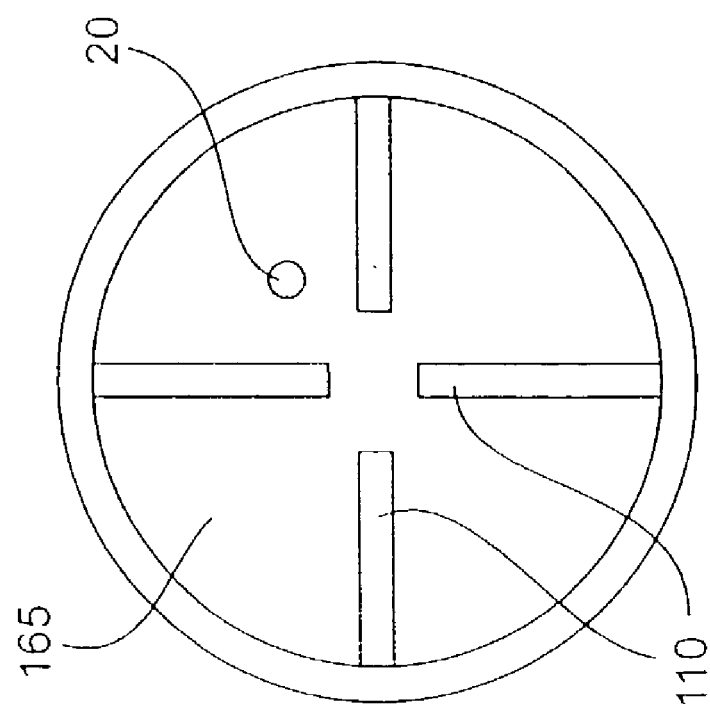
FIG. 15A is a view through the targeting optics of the laser beam delivery system prior to system calibration when the laser beam is directed to the fluorescing screen of FIG. 14.

In a second embodiment, measurement/alignment tool 100 comprises a screen 105 which fluoresces in response to laser light incident thereon, as illustrated in FIGS. 14 to 15B. Referring to FIG. 14, laser beam 18 is directed incident to screen 105, causing screen 105 to fluoresce in the region of beam spot 20. An operator 200 looking through targeting optics 122, (which preferably comprises a system microscope), views fluorescing of beam spot 20, as shown in FIG. 15A. Targeting optics 122 displays a reticle 110 to operator 200, and the operator adjusts the laser beam delivery optics so that the fluorescing beam spot is aligned with the reticle.

Advantageously, adjusting the location of beam spot 20 can be effected using the beam scanning mechanism. This may significantly facilitate alignment, as the system microscope need not be moved with a precise X-Y adjustment mechanism. Instead, the targeting signals transmitted to the galvanometric laser beam delivery optics can be selectively altered or offset to aim the beam tat the target location. Scanned accuracy may be enhanced by moving the beam between a plurality of target locations, and by individual beam shot targets using the signal offsets throughout the resculpting procedure. In alternative embodiments, the beam delivery optics may be mechanically adjusted to move beam spot 20 between the cross-hairs of reticle 110, thereby aligning the targeting optics of the laser beam delivery system.

In some embodiments, tool 100 may be removably positioned at or near the location which will be occupied by the eye during refractive resculpting. Tool 100 may be held by a swing-away arm or the like in a conventional manner. To set or check the system prior to a resculpting procedure, the operator enters an alignment mode. In this mode, reticle 110 remains stationary, and the laser fires to induce fluorescence at beam spot 20. The beam spot may be moved by the operator via an input device such as a joystick, mouse, switches, or the like which adjusts the beam delivery optics by changing the signal sent to the galvanometers. The laser beam would again fire producing a new laser spot 20, and the operator would continue to adjust the signal offsets until the laser beam is coincident with the laser beam. When coincidence is achieved, the operator can press a button (or provide any alternative signal to the system) and the system computer will then store the offset signals for determining the ablation center. Typically, the reticle will also be used to align the eye with the system after the tool is moved out of the way.

While the exemplary embodiments have been described in detail for clarity of understanding and by way of example, a variety of changes, adaptations, and modifications will be obvious for those of skill in the art. For example, a variety of scanning beam delivery systems might be used, including scanning systems which have a lens that may be variably offset from the beam axis or axes to image one or more laser beams at a laterally offset target location. The invention might be used with a wide variety of ablation planning protocols or algorithms, and provides input to such algorithms which can enhance their accuracy. Hence, the scope of the invention is limited solely by the appended claims.

What is claimed is:

1. A method of calibrating a scanning laser beam delivery system, the method comprising:
    positioning a calibration tool at a target location;
    directing a laser beam onto the tool with the scanning beam delivery system;
    sensing the laser beam using the tool;
    adjusting the scanning beam delivery system in response to the sensed laser beam; and
    directing the laser beam toward a patient's cornea and sculpting the cornea with the adjusted system.

2. The method of claim 1, wherein the scanning beam delivery system is a laser eye surgery system.

3. The method of claim 1, wherein a galvanometric mirror is used for directing the laser beam toward the patient's cornea.

4. The method of claim 1, further comprising removing the tool prior to sculpting the cornea with the adjusted system.

5. The method of claim 4, further comprising replacing the tool at the target location after sculpting the cornea, and repeating the directing, sensing and adjusting steps, wherein the directing step does not ablate the tool.

6. The method of claim 1, wherein directing the laser beam onto the tool comprises scanning the laser beam in a path across a reference-edge and onto a photodetector.

7. The method of claim 6, wherein sensing the scanned laser beam using the tool comprises measuring an output signal from the photodetector during the scanning, the output signal corresponding to an area of the laser beam incident on the photodetector during the scanning.

8. The method of claim 7, wherein sensing the scanned laser beam using the tool comprises determining dimensions of the laser beam by integrating an intensity of the photodetector signal output during the scanning.

9. The method of claim 7, wherein sensing the scanned laser beam using the tool comprises locating a center of the laser beam by determining when the output signal of the photodetector reaches half of a maximum output signal strength during the scanning.

10. The method of claim 9, wherein locating the center of the laser beam by determining when the output signal of the photodetector reaches a mid-point signal strength half-way between a first fraction of the maximum signal strength and a second fraction of the maximum signal strength, wherein the first and second fractions of the maximum signal strength add together to equal the maximum signal strength.

11. The method of claim 7, wherein sensing the scanned laser beam using the tool comprises determining a width of the laser beam in a direction of scanning by:

locating a leading edge of the laser beam by determining when the photodetector of the tool begins to emit an output signal indicative of the laser beam being incident thereon;

locating a trailing edge of the laser beam by determining when the output signal of the photodetector reaches a maximum output signal; and determining a spacing between the leading edge and the trailing edge of the laser beam.

12. The method of claim 1, wherein directing the laser beam onto the tool comprises scanning the laser beam across a target which fluoresces in response to the laser beam being incident thereon.

13. The method of claim 12, wherein sensing the scanned laser beam using the tool comprises viewing the fluoresced target through targeting optics of the laser beam delivery system.

14. The method of claim 13, wherein adjusting the system in response to the sensed laser beam comprises aligning laser beam delivery optics of the laser beam delivery system with the targeting optics until a viewed position of the fluoresced target is coincident with a target position of the targeting optics.

15. The method of claim 14, wherein the targeting optics of the laser beam delivery system comprises a reticle.

16. A method of calibrating a scanning laser beam delivery system, the method comprising:

positioning a calibration tool at a target location;

directing a laser beam onto the tool with the scanning beam delivery system;

sensing the laser beam using the tool;

adjusting the scanning beam delivery system in response to the sensed laser beam; and removing the tool and sculpting the cornea with the adjusted system.

17. The method of claim 16, further comprising replacing the tool at the target location after sculpting the cornea, and repeating the directing, sensing and adjusting steps, wherein the directing step does not ablate the tool.

18. A method of calibrating a scanning laser beam delivery system, the method comprising:

positioning a calibration tool at a target location;

directing a laser beam onto the tool with the scanning beam delivery system by scanning the laser beam in a path across a reference-edge and onto a photodetector;

sensing the laser beam using the tool; and adjusting the scanning beam delivery system in response to the sensed laser beam.

19. The method of claim 18, wherein sensing the scanned laser beam using the tool comprises measuring an output signal from the photodetector during the scanning, the output signal corresponding to an area of the laser beam incident on the photodetector during the scanning.

20. The method of claim 19, wherein sensing the scanned laser beam using the tool comprises determining dimensions of the laser beam by integrating an intensity of the photodetector signal output during the scanning.

21. The method of claim 19, wherein sensing the scanned laser beam using the tool comprises locating a center of the laser beam by determining when the output signal of the photodetector reaches half of a maximum output signal strength during the scanning.

22. The method of claim 21, wherein locating the center of the laser beam by determining when the output signal of the photodetector reaches a mid-point signal strength half-way between a first fraction of the maximum signal strength and a second fraction of the maximum signal strength, wherein the first and second fractions of the maximum signal strength add together to equal the maximum signal strength.

23. The method of claim 19, wherein sensing the scanned laser beam using the tool comprises determining a width of the laser beam in a direction of scanning by:

locating a leading edge of the laser beam by determining when the photodetector of the tool begins to emit an output signal indicative of the laser beam being incident thereon;

locating a trailing edge of the laser beam by determining when the output signal of the photodetector reaches a maximum output signal; and determining a spacing between the leading edge and the trailing edge of the laser beam.

24. A method of calibrating a scanning laser beam delivery system, the method comprising:

positioning a calibration tool at a target location;

directing a laser beam onto the tool with the scanning beam delivery system by scanning the laser beam across a target which fluoresces in response to the laser beam being incident thereon;

sensing the laser beam using the tool by viewing the fluoresced target through targeting optics of the laser beam delivery system; and adjusting the scanning beam delivery system in response to the sensed laser beam by aligning laser beam delivery optics of the laser beam delivery system with the targeting optics until a viewed position of the fluoresced target is coincident with a target position of the targeting optics.

25. The method of claim 24, wherein the targeting optics of the laser beam delivery system comprises a reticle.

* * * * *

UNITED STATES PATENT AND TRADEMARK OFFICE
CERTIFICATE OF CORRECTION

| | |
|---|---|
| PATENT NO. | : 7,001,375 B2 |
| APPLICATION NO. | : 10/383445 |
| DATED | : February 21, 2006 |
| INVENTOR(S) | : Kingman Yee et al. |

It is certified that error appears in the above-identified patent and that said Letters Patent is hereby corrected as shown below:

On the Title Page:

Please replace (73) with the following:

(73)    Assignee:    VISX, Inc. Santa Clara, CA (US)

Signed and Sealed this

Twenty-fourth Day of April, 2007

JON W. DUDAS
*Director of the United States Patent and Trademark Office*